(12) United States Patent
Tényi et al.

(10) Patent No.: US 9,855,381 B2
(45) Date of Patent: Jan. 2, 2018

(54) SOLUTION CIRCUIT APPARATUS WITH BYPASS, AND BLOOD PURIFICATION SYSTEM COMPRISING THE SOLUTION CIRCUIT APPARATUS

(71) Applicant: B. BRAUN AVITUM AG, Melsungen (DE)

(72) Inventors: Botond Tényi, Budakalász (HU); Peter Pózna, Budapest (HU)

(73) Assignee: B. BRAUN AVITUM AG, Melsungen (DE)

( * ) Notice: Subject to any disclaimer, the term of this patent is extended or adjusted under 35 U.S.C. 154(b) by 0 days.

(21) Appl. No.: 15/139,588

(22) Filed: Apr. 27, 2016

(65) Prior Publication Data

US 2016/0361485 A1 Dec. 15, 2016

(30) Foreign Application Priority Data

Jun. 10, 2015 (EP) .................................... 15171387

(51) Int. Cl.
*A61M 1/36* (2006.01)
*A61M 1/34* (2006.01)

(52) U.S. Cl.
CPC ............ *A61M 1/369* (2013.01); *A61M 1/342* (2013.01); *A61M 1/3403* (2014.02); *A61M 1/3424* (2014.02); *A61M 1/3437* (2014.02); *A61M 2205/3368* (2013.01); *A61M 2205/36* (2013.01); *A61M 2205/50* (2013.01)

(58) Field of Classification Search
CPC .. A61M 1/3403; A61M 1/342; A61M 1/3424; A61M 1/3437; A61M 1/369; A61M 2205/3368; A61M 2205/36; A61M 2205/50
See application file for complete search history.

(56) References Cited

U.S. PATENT DOCUMENTS

| | | | | |
|---|---|---|---|---|
| 4,844,074 A | * | 7/1989 | Kurucz | .................... F24H 1/121 236/91 F |
| 2008/0021377 A1 | * | 1/2008 | Kienman | ............ A61M 1/1696 604/29 |

(Continued)

FOREIGN PATENT DOCUMENTS

WO WO 2005/044339 5/2005

OTHER PUBLICATIONS

European Search Report for EP 15171387.2 dated Nov. 27, 2015.

*Primary Examiner* — Dirk Bass
(74) *Attorney, Agent, or Firm* — RatnerPrestia

(57) ABSTRACT

A solution circuit apparatus for a blood purification system having an extracorporeal blood circuit. The solution circuit apparatus includes a solution source; a warmer having a temperature sensor; a bypass branch; a delivery branch communicating with the extracorporeal blood circuit; a pump; a switch; and a control unit configured to set the solution circuit apparatus into one of a solution delivery condition and a solution stop condition. In the solution delivery condition the switch interrupts the bypass branch, and the pump delivers solution via the warmer and through the delivery branch. In the solution stop condition the switch interrupts the delivery branch, and the pump recirculates solution through the warmer via the bypass branch. In the therapy stop condition the pump rate is dependent on the output of the temperature sensor.

17 Claims, 1 Drawing Sheet

(56) References Cited

U.S. PATENT DOCUMENTS

2010/0038322 A1 2/2010 Hedmann et al.
2014/0217027 A1* 8/2014 Meyer .................... A61M 1/16
                                                                          210/646
2015/0114891 A1 4/2015 Meyer et al.

\* cited by examiner

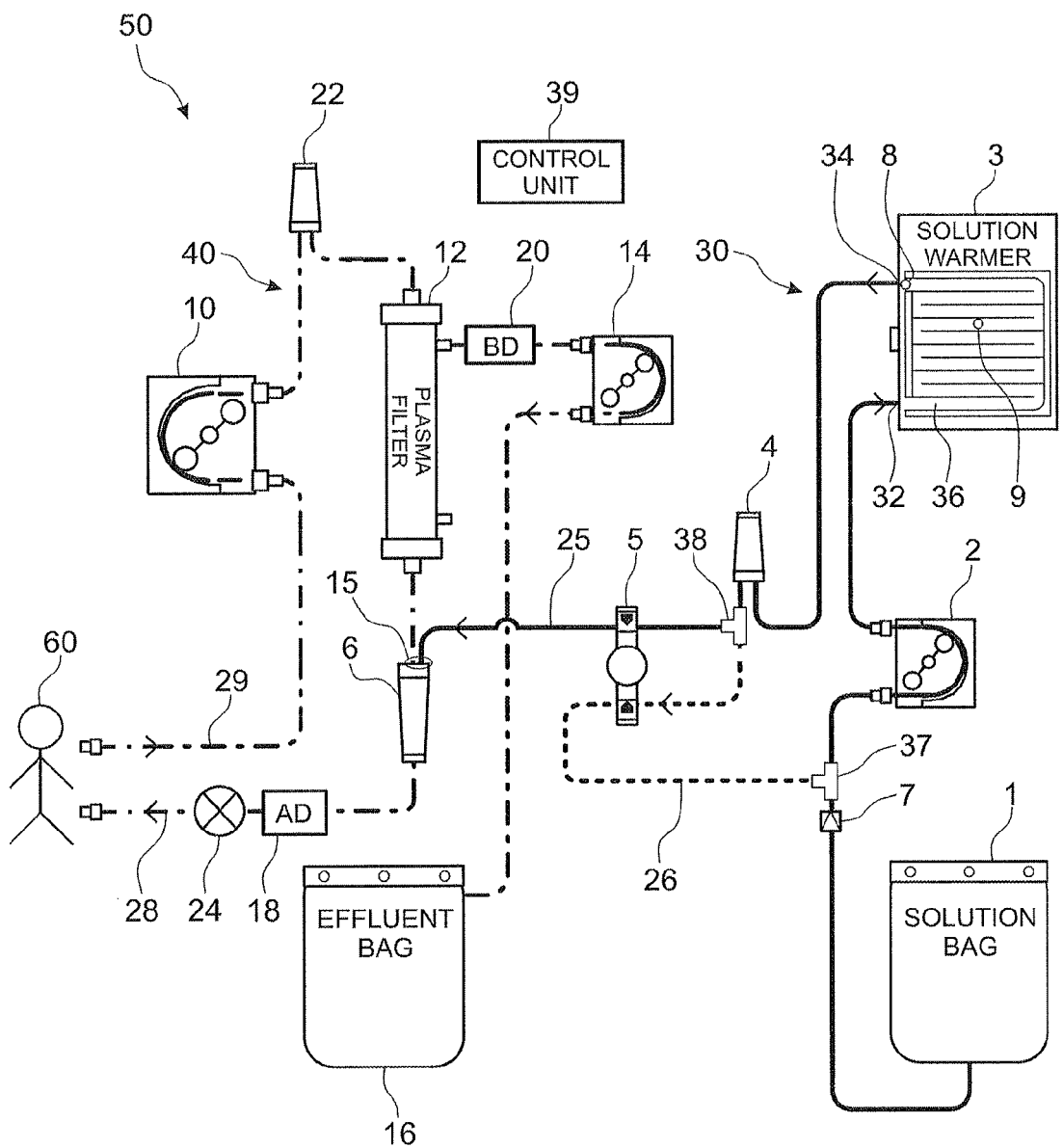

SOLUTION CIRCUIT APPARATUS WITH BYPASS, AND BLOOD PURIFICATION SYSTEM COMPRISING THE SOLUTION CIRCUIT APPARATUS

CROSS REFERENCE TO RELATED APPLICATIONS

This application claims priority to European application EP 15 171 387.2 filed Jun. 10, 2015, the contents of such application being incorporated by reference herein.

FIELD OF THE INVENTION

The invention relates to a solution circuit apparatus for a blood purification system or apheresis system (hereinafter called blood purification system), and a blood purification system comprising the solution circuit.

BACKGROUND OF THE INVENTION

Acute renal replacement therapy is a treatment for patients suffering from lost or reduced renal function, while apheresis therapy is a treatment for exchanging the plasma part of the blood. During the therapy, blood is led from the patient into an extracorporeal blood circuit, and metabolic waste products including uremic toxins and fluids, or plasma are removed from the blood. This involves the transfer of substances with convection and/or diffusion across a semipermeable membrane provided in a hemodialyzer or hemofilter or plasmafilter. The cleaned blood is then returned from the extracorporeal blood circuit to the patient.

In some blood purification therapies a solution fluid (dialysate) which comprises an aqueous solution of glucose and electrolytes is introduced from a solution circuit to the non-blood side of the semipermeable membrane.

Furthermore in some blood purification therapies any fluid lost during the therapy is partially or wholly replaced by the introduction of a solution fluid from the solution circuit directly into the blood in the extracorporeal blood circuit. In the cases of hemofiltration and plasma exchange therapy, the solution is substitution solution and plasma replacement solution respectively.

Hemodialysis, hemofiltration, and hemodiafiltration are renal replacement therapies which apply a hemodialyzer or hemofilter, while plasma exchange therapy applies a plasmafilter The dialysate, substitution solution or plasma replacement solution is hereinafter called solution. The hemodialyzer or hemofilter or plasmafilter is hereinafter called filter.

During a blood purification therapy one important task is to maintain the solution at a desired temperature before infusing it via the filter and/or introducing it directly into the blood, as the case may be. In clinical applications the solution is commonly provided in sterile bags which are stored at room temperature in a stock room of the clinic and are taken out when needed. The solution is then warmed to body temperature so as not to cool the patient's blood when the solution communicates with the blood either via the membrane of the filter, or directly via the extracorporeal blood circuit. Cooling of the blood in the extracorporeal blood circuit can lead to discomfort and, in the worst case, cardiac arrhythmia, which can occur especially when blood temperature falls below 33° C. It is known to warm the solution inline as it passes through the blood purification therapy equipment.

In order to maintain sterility the solution is conducted through a sterile disposable conduit or conduits, and there are known teachings for heating the solution with a warmer, wherein a heating element is provided to make contact on a surface of the disposable conduit. Thus the solution is heated inline, that is to say it is heated as it passes through the solution circuit, with thermal conduction. Temperature control is provided by temperature sensors placed preferably, for reasons of cost, externally to the disposable conduit, rather than directly in contact with the solution.

In the case of these known warmers the heating element has a high thermal inertia, in particular since it tends to have a large heating surface. Also the temperature of the heating element surface must be higher than the desired solution temperature in order to ensure efficient heat flow. In the case that the solution delivery is stopped by the user or by an alarm signal, for example, there is the possibility of temporary and local overheating of the solution even when power to the warmer is stopped. At this time the respective temperatures of the solution and heating element are equalizing. Therefore a situation can occur when the solution temperature is uncontrolled. Various operating factors influence the possibility and degree of overheating of the solution, such as surface temperature of the heating element, ambient air temperature, temperature of the sterile bag, and desired solution temperature. Overheating of the solution can lead to thermal breakdown of the solution and/or thermal hemolysis of the patient's blood.

DESCRIPTION OF THE RELATED ART

WO 2005 44339 A2 discloses a dialysis apparatus having a solution circuit and an extracorporeal blood circuit. The solution circuit has an inline heater through which solution is conveyed to a dialyzer with a solution pump. The solution circuit has a recirculation branch for bypassing the dialyzer, wherein solution that is at too high a temperature may be diverted and prevented from reaching the dialyzer and consequently the extracorporeal blood circuit.

The apparatus disclosed in WO 2005 44339 A2 serves to ensure that overheated solution does not reach the patient. However there is still the chance of the solution overheating, for the reasons given above. This is especially critical in the case of plasma exchange therapy wherein the solution is configured as plasma which can become compromised when overheated, e.g. undergo permanent and undesirable changes such as protein denaturation.

Overheated solution is solution that is heated to a temperature condition that is hazardous to the solution and/or hazardous to the patient. The temperature condition may be time dependent.

A blood purification system having a solution circuit according to the preamble of the independent claim is known from US 2015/114891 A1.

SUMMARY OF THE INVENTION

It is an object of the invention to provide a solution circuit for a blood purification system, which reduces the chance of overheating of the solution, when the solution flow is stopped. It is a further object of the invention to provide a blood purification system comprising said solution circuit.

An object is solved by a solution circuit having the features of the independent claim, and by a blood purification system having the features of a dependent claim. Preferable embodiments are set forth in the dependent claims.

According to a first aspect of the invention, a solution circuit apparatus is provided for a blood purification system, preferably an acute blood purification system, comprising said solution circuit apparatus and an extracorporeal blood circuit. The solution circuit apparatus comprises: a solution source; a warmer (-means) having a temperature sensor; a bypass branch; a delivery branch configured to communicate with the extracorporeal blood circuit; a pump (-means) which is preferably configured for conveying solution from the solution source and through the solution circuit apparatus; a switching means or device; and a control unit or means configured to set the solution circuit apparatus into one of a solution delivery condition and a solution stop condition. In the solution delivery condition the switching means (device) interrupts/blocks the bypass branch and solution is delivered through the warmer and the delivery branch with the pump. In a solution stop condition the switching means (device) interrupts/blocks the delivery branch and solution is recirculated through the warmer and the bypass branch with the pump. In at least the solution stop condition the pump rate is dependent on the output of the temperature sensor.

As a result the solution circuit apparatus delivers warmed solution to the extracorporeal blood circuit, in the solution delivery condition. The temperature of the solution is controlled by the control unit with the warmer. In the solution delivery condition the bypass branch is interrupted which means that all of the solution pumped by the solution pump is delivered to the extracorporeal blood circuit via the delivery branch. When the solution circuit apparatus is in a solution stop condition, for example when the user temporarily stops the therapy or the solution stop condition is triggered by a system alarm, the delivery branch is interrupted. Even though solution is no longer delivered to the extracorporeal blood circuit, solution continues to circulate through the warmer with the bypass branch. Therefore solution is less likely to overheat compared to a comparative apparatus wherein the solution flow through the warmer stops in the solution stop condition. At the same time the heater is cooled by transferring heat to the environment via the recirculating solution. Furthermore because the pump rate in the solution stop condition is controlled based on the temperature measured at the temperature sensor, recirculation of solution through the warmer may be further optimized to further reduce the chance of overheating.

According to a second aspect of the invention the solution circuit apparatus of the first aspect of the invention may be provided wherein, in the solution stop condition, the solution flow bypasses the solution source. Bypassing of the solution source is ensured preferably with a non-return valve, or check valve, which may be arranged in a branch connecting the solution source with the solution circuit apparatus and allowing only a fluid flow from the solution source.

As a result the solution is not able to return to the solution source. The risk of thermal or biological contamination is reduced. For blood purification therapies that require accurate monitoring of the net fluid removal from the patient, the chance of an error in the monitoring of the quantity of fluid entering the extracorporeal blood circuit is reduced.

According to a third aspect of the invention the solution circuit apparatus of the first or second aspect of the invention may be provided, wherein fluid communication in the solution circuit apparatus is with separate flexible disposable tubes.

As a result the solution circuit apparatus may be assembled using low cost tubing which is commonly available. The construction and assembly is less complicated than a comparative example using a cassette based system. Flexible tubes facilitate routing and can be used with pinch valves, for example, which reduces the risk of contamination or leaks.

According to a fourth aspect of the invention the solution circuit apparatus may be provided wherein the warmer has an inlet for receiving solution, an outlet for discharging solution, and a preferably disposable heated passage in thermal contact with a heating element.

As a result the solution may be heated by the warmer without leaving the solution circuit. The warmer interfaces with the solution circuit via the inlet and the outlet. This facilitates a modular construction of the solution circuit apparatus. Furthermore the solution is kept separate from the heating element with the heated passage. The heated passage is disposable so the heating element may be reused over successive treatments without contamination risk.

According to a fifth aspect of the invention, the solution circuit apparatus may be provided wherein the heating element is planarly formed and the heated passage is configured as a bag with a meander flow path.

As a result of the planar heating element, the heat transfer to the heated passage is improved. The meander flow path further improves efficiency of the warmer. Since the disposable heated passage is configured as a bag, it may be configured to have an arbitrary wall thickness which is preferably less than the disposable tubing used elsewhere in the solution circuit apparatus. Therefore a less powerful warmer is required. The temperature difference between the heating element and the heated passage, which is required to ensure sufficient conductive heat flow, can be reduced so that the chance of overheating of the solution in the solution stop condition is reduced.

According to a sixth aspect of the invention the solution circuit apparatus may be provided wherein the heating element is cylindrically formed and the heated passage is configured as disposable tubing that surrounds the heating element, preferably helically wrapped around the heating element.

As a result the warmer of the present aspect is less planarly expansive than a warmer with a planar heating element, while the surface area of the heating element does not need to be reduced, thus saving space. Since the heated passage is configured as disposable tubing, the construction of the solution circuit apparatus is simpler. The rate of heat transfer may optionally be adapted during treatment setup by selecting the number of helical turns of the disposable tubing around the cylindrical heating element.

According to a seventh aspect of the invention the solution circuit apparatus may be provided wherein the heated passage is configured as disposable tubing and the heating element surrounds the disposable tubing.

Because the heated passage is surrounded by the heating element, efficiency of heat transfer may be improved.

According to an eighth aspect of the invention the solution circuit apparatus may be provided wherein a first temperature sensor is provided at the warmer outlet.

The first temperature sensor may be used for accurate control of the solution leaving the warmer, which helps to ensure that the solution leaving the warmer does not exceed a hazardous temperature level.

According to a ninth aspect of the invention the solution circuit apparatus may be provided wherein a second temperature sensor is provided on the heated passage.

The second temperature sensor on the heated passage may be used to control the temperature of solution in the warmer. Due to variation in the temperature of the solution along the heated passage, this temperature sensor is able to detect overheated solution in the heated passage. This solution would remain undetected by a comparative solution circuit having a temperature sensor only at the outlet or the inlet of the warmer. This is because in some conditions solution may overheat in some regions as it passes through the heated passage, and then cool down before it reaches the outlet of the warmer. This is particularly advantageous in the case of plasma exchange therapy, wherein the solution can become compromised when overheated.

Since the temperature over the surface of the heating element is usually not uniform it can be advantageous to determine the solution temperature over the heating element. Accordingly it is preferable if the solution circuit apparatus is provided with both of the temperature sensors described above, further preferably more than these two. For example one temperature sensor may be arranged at the heater outlet and several temperature sensors may be arranged to be distributed along the heated passage.

According to a tenth aspect of the invention the solution circuit apparatus may be provided wherein, in the solution stop condition, the pump rate is controlled mainly to eliminate reaching overheating criteria or based on whether a first overheating criterion is satisfied, the first overheating criterion being satisfied when the temperature measured at one temperature sensor, or optionally more than one temperature sensor, exceeds, over any time duration, a first predetermined threshold temperature value.

As a result the solution flow rate through the warmer may be optimized to reduce the chance that the solution becomes overheated.

According to an eleventh aspect of the invention the solution circuit apparatus may be provided wherein in the solution stop condition the pump rate is controlled mainly to eliminate reaching overheating criteria or based on whether a second overheating criterion is satisfied, the second overheating criterion being satisfied when the temperature measured at one temperature sensor, or optionally more than one temperature sensor, exceeds a second predetermined threshold temperature value for longer than a predetermined threshold time duration.

As a result the solution flow rate through the warmer may be further optimized to reduce the chance that the solution becomes overheated. Additionally the solution circuit apparatus will not raise a false alarm or take unnecessary steps to avoid overheating if the solution reaches a high temperature for a limited period of time which is not an overheating condition.

According to a twelfth aspect of the invention the solution circuit apparatus may be provided wherein the switching means is provided either as a single pinch valve (2-way valve) on the bypass branch and a single pinch valve (2-way valve) on the delivery branch; or as a switch valve with two lines (4-way valve) configured to interrupt alternately one of the bypass branch and the delivery branch. Further preferably the valves are configured as pinch valves.

As a result the solution circuit apparatus may be assembled using low cost valves which are commonly available. The construction and assembly is less complicated than a comparative example using a customized valve system based on a cassette. Pinch valves may preferably be used. In particular the provision of a switch valve with two lines (4-way valve) saves space compared to separate single pinch valves (2-way valves). Because the switch valve with two lines (4-way valve) prevents a situation when both branches are open or closed correct operation of the solution circuit apparatus is further ensured.

According to a thirteenth aspect of the invention a blood purification system is provided comprising: the solution circuit of any one of the first to twelfth aspects; and an extracorporeal blood circuit. In said aspect the control unit is further configured to set the blood purification system into one of a therapy delivery condition and a therapy stop condition. The therapy delivery condition comprises the solution delivery condition. The therapy stop condition comprises the solution stop condition. The blood purification system is preferably configured as an acute blood purification system.

By incorporating the solution circuit apparatus into a blood purification system, preferably an acute blood purification system, construction is simplified. In particular the control unit may be configured to control and set conditions of the solution circuit apparatus as well as to control and set conditions of the blood purification system blood purification system. This means that all elements of the blood purification system such as pumps, valves and sensors may communicate electrically with a single control unit.

According to a fourteenth aspect of the invention the blood purification system may be configured for performing plasma exchange therapy, pre- and/or post-dilution hemofiltration, pre- and/or post-dilution hemodiafiltration or hemodialysis. The features of the blood purification system of the fourteenth aspect of the invention are not limited to one particular type of blood purification therapy but can be configured by the skilled person to suit the particular therapy.

BRIEF DESCRIPTION OF THE DRAWING

The invention is best understood from the following detailed description when read in connection with the accompanying drawing. Included in the drawing is the following FIGURE:

FIG. 1—a schematic layout of a plasma therapy exchange apparatus according to an embodiment example of the invention.

DETAILED DESCRIPTION OF THE PREFERRED EMBODIMENTS

FIG. 1 shows a plasma exchange apparatus 50 comprising the following structural features. An extracorporeal blood circuit 40 is in fluid communication with a solution circuit 30 (solution circuit apparatus). In the present embodiment example the fluid connections are configured from flexible plastic disposable tubing of a type known to the skilled person. The fluid connections of the extracorporeal blood circuit and effluent circuit are shown in FIG. 1 with dash-dot lines. The fluid connections of the solution circuit apparatus are shown in FIG. 1 with solid lines and dashed lines.

The extracorporeal blood circuit 40 is configured to be fluidly connectable to a patient 60 with a venous line 28 and an arterial line 29. The arterial line 29 is fluidly connected to a plasma filter 12 via a blood pump 10 and then a first degassing chamber 22. The plasma filter 12 comprises a semipermeable membrane (not shown). The plasma filter 12 is configured to receive blood on one side of the semipermeable membrane. A first exit is provided on the one side of the semipermeable membrane. A second exit is provided on the other side of the semipermeable membrane and is fluidly connected to an effluent bag 16 via an effluent pump 14 and a blood leak detector 20. The second exit is fluidly connected to a venous chamber 6. Here a joining point 15 is provided wherein the solution circuit 30 is fluidly connected to the extracorporeal blood circuit 40. That is to say, the other end of a delivery branch 25 (discussed later) is fluidly connected to the extracorporeal blood circuit 40 at the joining point 15. The outlet of the venous chamber 6 is fluidly connected to the venous line 28 via an air detector 18 that communicates with the control unit 39 and a venous pinch valve 24 which communicates with the control unit 39.

The solution circuit apparatus 30 has a solution bag 1 (solution source) which comprises fresh plasma substitution solution (solution). The solution bag 1 is fluidly connected, preferably via a non-return valve 7, to a first T-junction 37. The first T-junction 37 is further fluidly connected to a solution pump 2 which in turn is fluidly connected to the inlet 32 of a warmer 3.

The warmer 3 comprises the inlet 32, an outlet 34, at least one heating element (not shown), and a heated passage 36. The inlet 32 is fluidly connected to the outlet 34 via the heated passage 36. At least one side of the heated passage 36 contacts the at least one heating element which is configured to be heated by electrical power.

The warmer 3 further comprises two temperature sensors 8, 9. A first temperature sensor 8 is arranged at the warmer outlet 34 so as to contact the outside of the warmer outlet 34. The first temperature sensor 8 is alternatively arranged on the outside of the disposable tubing that is fluidly connected to the heated passage 36, near the warmer outlet 34, or on the outside of the heated passage 36 near the warmer outlet 34. The second temperature sensor 9 is arranged further away from the warmer outlet 34, towards the heated passage, so as to contact the outside of the heated passage 36, preferably at the intermediate point along the meander flow path of the heated passage 36. The temperature sensors 8, 9 may comprise thermocouples, thermistors, infra-red sensors or other suitable devices known to the skilled person.

In the present embodiment example the heater is configured as an electrically powered plate warmer with one resistive heating element, preferably two resistive heating elements, with one element on each side of the heated passage 36. The heated passage 36 is provided as a disposable plastic bag having a meander flow path on its inside. The wall thickness of the heated passage 36 is preferably less than the thickness of the disposable tubing. The heating element has a planar heating surface which makes thermally conductive contact with the outside of the heated passage 36. The heating element may comprise metal, ceramic or other suitable material as planar thermal contact to the heated passage 36.

The outlet of the warmer 3 is fluidly connected via a degassing chamber 4 to one port of a second T-junction 38. The remaining two ports are fluidly connected to the delivery branch 25 and a bypass branch 26 respectively. The path of the bypass branch is shown in FIG. 1 with a dashed line. The delivery branch 25 and the bypass branch 26 are each configured as a flexible tube length having two ends. The delivery branch 25 is fluidly connected to the second T-junction 38 at the delivery branches one end. The other end of the delivery branch 25 makes fluid connection with the extracorporeal blood circuit 40 at the joining connection 15. One end of the bypass branch 26 is fluidly connected to the second T-junction 38. The other end of the bypass branch 26 is fluidly connected to the first T-junction 37.

A recirculation route is formed by the following elements and their fluid connections: bypass branch 26, first T-junction 37, solution pump 2, warmer 3, and second degassing chamber 4.

A switch valve with two lines or a 4-way pinch valve 5 (switching means) is provided on the bypass branch 26 and the delivery branch 25. The 4-way pinch valve 5 has a first passage and a second passage and is configured to be in one of two states. The 4-way pinch valve 5 is configured, in a first state, to open the first passage and interrupt the second passage and, in a second state, to interrupt the second passage and open the first passage. In other words the 4-way pinch valve 5 is configured to open the first or second passage while blocking the other one of the first and second passages. The delivery branch 25 forms the first passage and the bypass branch 26 forms the second passage. That is to say a location on the flexible tube that forms the bypass branch 26 is configured to be interrupted by the 4-way pinch valve 5 to interrupt flow through the first passage and a corresponding location on the flexible tube that forms the delivery branch 25 is configured to be interrupted by the 4-way pinch valve 5 to interrupt flow through the second passage. Further preferably the 4-way pinch valve is solenoid activated wherein the second passage is closed in the rest position. Further features of the 4-way pinch valve 5 are known to the skilled person.

A control unit 39 is provided to control the operational elements of the solution circuit 30, that is to say the control unit 39 is configured to control at least the solution pump 2; the warmer 3; and the 4-way pinch valve 5 based on outputs from the first 8 and second 9 temperature sensors and on operational modes selected by the user. Furthermore the control unit may set one of the solution delivery condition and the solution stop condition. The control unit 39 may comprise a control panel (not shown).

The above-described pumps 2, 10, 14 are preferably configured as peristaltic pumps, the disposable tubing providing the respective flexible hose for each pump 2, 10, 14.

The operation of the plasma exchange apparatus 50 is described in the following. A therapy delivery condition is set by the user via the control panel. The therapy delivery condition includes a solution delivery condition, and comprises the following processes. Blood from the patient 60 is conveyed into the extracorporeal blood circuit 40 through the arterial line 29 by the blood pump 10. The blood passes first to the first degassing chamber 22 which removes gas bubbles from the blood, and then to the plasma filter 12. The plasma filter 12 receives the blood and separates the plasma with its semipermeable membrane, facilitated by the pressure difference provided by the blood pump 10 and the effluent pump 14. The separated plasma exits the plasma filter 12 from an exit and passes via the blood leak detector 20, then the effluent pump 14 and then into an effluent bag 16. The rest of the blood, which is now concentrated blood, does not pass through the semipermeable membrane, and it discharges from a second plasma filter exit. Thus plasma is removed from the extracorporeal blood circuit 40 while concentrated blood remains in the extracorporeal blood circuit 40. Upon detection of blood the blood detector 20 sends an alarm signal to the control unit 39

The concentrated blood exits the plasma filter 12 where it joins with a flow of solution (described later) at the joining point 15. The combined flow enters the venous chamber 6 and then passes sequentially to an air detector 18, a non-return valve 7, and then back to the patient 60 via the venous line 28. Thus the plasma exchange apparatus 50 removes blood from the patient 60, replaces the plasma in the blood with solution, and returns the treated blood to the patient 60. Upon detection of air the air detector 18 sends an alarm signal to the control unit 39.

A therapy delivery condition of the plasma exchange apparatus 50 includes a solution delivery condition of the solution circuit apparatus 30. In the solution delivery condition the solution circuit apparatus 30 is configured to perform the following processes. Solution is conveyed from the solution bag 1 via the non-return valve 7 and though the solution pump 2. The pump rate of the pump 2 is controlled by the control unit 39. At this stage the solution is typically below body temperature, for example room temperature. From there it enters the warmer 3 via the warmer inlet 32 and into the inner side of the heated passage 36 which has the meander passage. On instruction from the control unit 39, electrical power is sent to the warmer 3 which causes its heating element to heat up, thus conductively transferring heat through the heated passage 36 to the solution. The control unit 39 is configured to determine the necessary heater power to achieve the required solution temperature (required temperature of the solution as it exits the warmer 3) in consideration of the pump rate of the solution pump 2 and the outputs of the temperature sensors 8, 9, preferably the first temperature sensor 8. In particular the required solution temperature is a temperature range that includes body temperature.

The heated solution leaves the warmer 3 via the warmer outlet 34 and passes through the second degassing chamber 4 for removing gas bubbles from the solution. When the solution circuit apparatus 30 is in the solution delivery condition, the control unit 39 actuates the 4-way pinch valve 5 to the first state, interrupting the bypass branch 26 and opening the delivery branch 25. Thus when the heated solution reaches the second T-junction 38, access through the bypass branch 26 is blocked and access to the delivery branch 25 is opened, so the heated solution enters the delivery branch 25, passes through the open (first) passage of the 4-way pinch valve 5, and enters the extracorporeal blood circuit 40 via the joining point 15 where it joins with the flow of concentrated blood exiting the plasma filter 12, as described above. Thus the 4-way pinch valve 5 closes the entry to the blood and opens a bypass circuit comprising the warmer 3.

The control unit 39 changes the condition of the plasma exchange apparatus 50 from a therapy delivery condition to a therapy stop condition, for example when therapy is stopped by the user, or when the control unit 39 receives an alarm signal from at least one of the air detector 18, blood detector 20, or either temperature sensor 8,9. At the same time the control unit 39 changes the solution circuit apparatus 30 from the solution delivery condition to the solution stop condition. A therapy stop condition of the plasma exchange apparatus 50 includes a solution stop condition of the solution circuit apparatus 30. The solution stop condition describes a condition wherein the flow of solution out of the solution circuit 30 is stopped.

In the solution stop condition the solution circuit apparatus 30 is configured to perform the following processes. The control unit 39 actuates the 4-way pinch valve 5 to the second state, opening the bypass branch 26 and interrupting the delivery branch 25. Thus when the heated solution reaches the second T-junction 38, access through the bypass branch 26 is opened and the access to the delivery branch 25 is closed, so the heated solution enters the bypass branch 26, passes through the open passage of the 4-way pinch valve 5, and rejoins the solution circuit 30 via the first T-junction 37, after which it enters the solution pump 2. The non-return valve 7 prevents the heated solution from flowing into the solution bag 1. In this way the heated solution recirculates around the solution circuit 30, conveyed by the solution pump 2, and does not enter the extracorporeal blood circuit 40, nor the solution bag 1. Solution at a temperature above ambient temperature is cooled by the environment as it passes through the tubing of the solution circuit 30. Thus in a solution stop condition the flow of solution into the extracorporeal blood circuit 40, and thus the patient 60, is stopped. Advantageously the flow of solution inside the warmer 3 is not stopped. It is preferable that the control unit 39 reduces or further preferably totally interrupts power to the heating element during the solution stop condition. In this way the cooling by the environment is facilitated and the possibility that the solution overheats during the solution stop condition is further reduced.

It is preferable to control the solution flow rate during the solution stop condition so as to optimize the cooling of the solution temperature, as is described in the following. The pump rate of the solution pump 2 is controlled by the control unit 39 and, in the solution stop condition, may be dependent on the respective outputs of the first 8 and second 9 temperature sensors. Preferably the pump rate of the solution pump 2 in the solution stop condition is controlled mainly to eliminate reaching overheating criteria or based additionally on whether a first overheating criterion and a second overheating criterion are satisfied. The first overheating criterion is satisfied when the temperature measured at one or both of the first 8 and second 9 temperature sensors exceeds, for any time duration, a first predetermined threshold temperature value which preferably corresponds to a momentary hazardous temperature. The second overheating criterion is satisfied when the temperature measured at one or both of the first 8 and second 9 temperature sensors exceeds a second predetermined threshold temperature value for longer than a predetermined threshold time duration. The second overheating criterion preferably corresponds to a time-dependent hazardous temperature which is maintained for a corresponding hazardous time duration. Further preferably the first predetermined threshold temperature value may be set to be higher than the second predetermined threshold value. For example, the first predetermined threshold temperature value may be set to 46° C., the second predetermined threshold temperature value may be set to 42° C., and the predetermined threshold time duration may be set to a particular time duration within a range of one to seven seconds, further preferably two to five seconds. The pump rate of the solution pump 2 in the solution stop condition may be controlled based on one or both of the respective outputs of the first 8 and second 9 temperature sensors, and one or both of the first and second overheating criteria. The required pump rate may be determined by a feedback loop within the control unit 39. In conclusion, the solution circulates around the solution circuit 30 with an optimal flow rate, wherein the solution is continuously cooled by the ambient temperature external to the disposable tubing. Therefore an optimal pump rate of the solution pump 2 is determined by temperature measurement in the heated passage 36 and preferably at the warmer outlet 34. Depending on the solution the reaction can be different. In case of plasma exchange reaching the first threshold temperature or the second threshold temperature above the threshold time means that the therapy cannot be continued, but the replacement solution shall be exchanged. In case of dialysate solutions the therapy can be continued, if the solution temperature is below any of the threshold temperatures.

It is noted that when the solution pump 2 operates, it preferably conveys solution through the warmer 3 and further preferably the second degassing chamber 4, not only when the bypass branch 26 is open and the delivery branch 25 is closed, but also when the delivery branch 25 is open and the bypass branch 26 is closed, i.e. in both a solution stop condition and a solution delivery condition.

In a preferable modification of the present embodiment example, in the solution stop condition and preferably also in the solution delivery condition, the control unit 39 produces an alarm signal when the output of one of the temperature sensors 8, 9 satisfies one or both of the first and the second overheating criteria. This is particularly advantageous in the case of plasma exchange therapy wherein the solution is plasma substitution solution which undergoes irreversible damage when overheated. In the case of treatments other than plasma exchange therapy, the invention has an advantage that the solution flow can be started sooner after the user requests resumption of treatment, in comparison with a comparative therapy apparatus that performs solution recirculation only as a failsafe procedure during therapy delivery, and not when therapy is paused. Therefore total treatment time is reduced.

A return to the therapy delivery condition is conditional on the user continuing the therapy and/or all alarm signals being cancelled or not present. The return to the therapy delivery condition comprises returning to the solution delivery condition, wherein the control unit 39 actuates the 4-way pinch valve 5 to the second state, opening the bypass branch 26 and interrupting the delivery branch 25.

Flow of solution from the solution circuit 30 to the extracorporeal blood circuit 40 may preferably restart on condition that the neither of the first and second overheating criteria is satisfied.

The advantages of the embodiment example are detailed in the following. The solution flow rate is controlled to result in optimal cooling by the environment. The chance of solution being overheated, when the solution flow is stopped during therapy, is reduced. A comparative example solution circuit 30 that has a recirculation route for use only as a failsafe during the solution delivery condition, and does not recirculate solution through the warmer in a solution stop condition, would not reduce the chance of overheating.

Furthermore the solution flow rate is controlled based on the output of the temperature sensors. This improves temperature control of the solution.

In the solution stop condition, when overheating is unlikely, the pump rate of the solution pump 2 may be reduced and energy efficiency of the solution circuit apparatus 30 is thereby improved.

When the solution delivery condition is resumed, for example when therapy delivery is resumed, the solution is in a safe temperature range for therapy to continue. The user does not have to wait for recirculation to be performed, which would delay the restart of the therapy.

The provision of two temperature sensors at different places in the solution circuit 30 ensures reliable and accurate temperature sensing. This is especially important in the case of plasma exchange therapy, where the solution is plasma replacement solution which should not be overheated. The first temperature sensor 8 serves to ensure that the delivery temperature of the solution is within a suitable range. The second temperature sensor 9 serves to reduce local overheating of the solution.

When the heated passage 36 is provided as a bag with a thinner wall than the disposable tube, heat transfer to the solution is more efficient and the chance of overheating is reduced.

The recirculation route preferably bypasses the solution bag 1. Thus solution recirculates without returning to the solution bag 1. The non-return valve 7 further ensures that solution does not return to the solution bag 1, reducing the risk of contamination of fresh solution, and also reducing errors in the monitoring of net fluid removal. Also the construction is simpler than a comparative example in which the solution bag 1 and/or drain is included in the recirculation route. Likewise the recirculation route bypasses the delivery branch 25 and the effluent bag 16. The present embodiment does not waste fresh solution in order to cool the heater. A comparative example, for instance a hemodialysis device that continuously conveys fresh solution from the solution bag 1, through the warmer 3 and to an effluent bag 16 in order to cool the heater, would waste fresh solution.

The present embodiment uses standard connection elements, namely disposable plastic flexible tubing, and standard valves and connectors, e.g. T-junctions 37, 38. Therefore the solution circuit apparatus 30 is easy to assemble and has a simpler construction compared to cassette based systems which are configured as non-standard custom assemblies. The 4-way pinch valve 5 of the present embodiment ensures reliable transition between the solution delivery and solution stop conditions.

The invention is not limited to the features of the embodiment example, but by the scope of the claims. The following alternative features are in accordance with the invention.

The 4-way pinch valve 5 and the second T-junction 38, being standard parts, may be replaced by a 3-way pinch valve which is also a commonly used standard part. Therefore part count is reduced. Alternatively the switch valve with two lines (4-way pinch valve) 5 may be replaced by two switch valves with one line, respectively (2-way pinch valves), in other words one 2-way pinch valve on the bypass branch 26 and delivery branch 25, respectively. Preferably, the alternating operation of the 2-way pinch valves may be ensured by the control unit 39. Further preferably, the 2-way pinch valves on the bypass branch 26 and the delivery branch 25 may be the same type as the venous pinch valve 24, which reduces the range of parts.

In FIG. 1 the non-return valve 7 is arranged closely upstream of the first T-junction 37. According to aspects of the invention the non-return valve 7 may be anywhere downstream of the solution bag 1 provided that it prevents any flow from the solution circuit 30, including the bypass branch 26, to the solution bag 1. For example it could be incorporated into the first T-junction 37 or incorporated into the outlet of the solution bag 1.

The present embodiment is configured as a plasma exchange apparatus, but the invention may be applied to pre-dilution hemofiltration, pre- and/or post-dilution hemofiltration, pre- and/or post-dilution hemodiafiltration or hemodialysis. Accordingly variations within the scope of the claims are possible that incorporate other elements of blood purification systems known to the skilled person, such as pressure transducers within the extracorporeal blood circuit 40 and/or solution circuit 30, and conductivity sensors in the solution circuit 30. Net fluid removal from the patient 60 may be monitored using methods known in the art such as with flow meters, balancing means or weighing scales. The control unit 39 may be configured to communicate with these sensors. Accordingly the triggering of an alarm signal from the control unit 39 may be based on the outputs from these sensors.

In the embodiment example the heated passage 36 is formed from a disposable plastic bag having a meander flow path. However in a first alternative warmer configuration, the heated passage 36 may be configured from disposable tubing instead. Furthermore the heating element of the embodiment example has a planar heating surface. However in a second alternative warmer configuration, the heating element may be cylindrically formed. The heated passage 36, when formed as disposable tubing in particular, may be helically wrapped several times around the heating element, making thermal contact with the heating element.

In the present embodiment the warmer 3 is arranged downstream of the solution pump 2. However the invention is not limited by this arrangement, and the pump may be arranged downstream of the warmer. Advantages of the invention may be achieved when the pump is configured to convey solution from the solution bag to the warmer, in both the solution delivery condition and the solution stop condition.

According to aspects of the invention it is possible to reduce the overheating effect on solution, in a situation when the solution flow is stopped during blood purification therapy.

The invention claimed is:

1. A solution circuit apparatus of a blood purification system comprising:
    a solution source;
    a warmer having a temperature sensor;
    a bypass branch;
    a delivery branch configured to communicate with an extracorporeal blood circuit;
    a pump for conveying solution at a pump rate from the solution source and through the solution circuit apparatus;
    a junction comprising:
        a first port connected to a fluid line leading from the warmer,
        a second port connected to an end of the bypass branch, and
        a third port connected to an end of the delivery branch;
    a switching device separate from the junction comprising at least one valve configured to interrupt alternately one of the bypass branch and the delivery branch; and
    a control unit configured to set the solution circuit apparatus into one of a solution delivery condition and a solution stop condition, wherein
        in the solution delivery condition the control unit controls the switching device to interrupt the bypass branch using the at least one valve such that solution is delivered through the warmer and the third port of the junction into the delivery branch by the pump; and
        in the solution stop condition the control unit controls the switching device to interrupt the delivery branch using the at least one valve such that solution is directed through the second port of the junction into the bypass branch and is recirculated through the warmer and the bypass branch by means of the pump, wherein in the solution stop condition the control unit controls the pump such that the pump rate is dependent on temperature of the solution at the temperature sensor.

2. The solution circuit apparatus of claim 1 wherein in the solution stop condition the solution bypasses the solution source.

3. The solution circuit apparatus of claim 1, wherein communication within the solution circuit apparatus is through separate flexible disposable tubes.

4. The solution circuit apparatus of claim 1, wherein the warmer has an inlet for receiving solution, an outlet for discharging solution, and a heated passage in thermal contact with a heating element.

5. The solution circuit apparatus of claim 4, wherein the heating element is planarly formed and the heated passage is configured as a bag with a meander flow path.

6. The solution circuit apparatus of claim 4, wherein the heating element is cylindrically formed and the heated passage is configured as disposable tubing that surrounds the heating element.

7. The solution circuit apparatus of claim 6, wherein the disposable tubing is helically wrapped around the heating element.

8. The solution circuit apparatus of claim 4, wherein the heated passage is configured as disposable tubing and the heating element surrounds the disposable tubing.

9. The solution circuit apparatus of claim 4, further comprising:
    a first temperature sensor provided at the warmer outlet.

10. The solution circuit apparatus of claim 9, further comprising:
    a second temperature sensor provided on the heated passage.

11. The solution circuit apparatus of claim 1, wherein in the solution stop condition the control unit controls the pump such that the pump rate is optimized to eliminate reaching overheating criteria.

12. The solution circuit apparatus of claim 1, wherein in the solution stop condition the control unit controls the pump such that the pump rate is optimized based on whether a first overheating criterion is satisfied, the first overheating criterion being satisfied when the temperature measured at a temperature sensor exceeds, over any time duration, a first predetermined threshold temperature value.

13. The solution circuit apparatus of claim 12, wherein in the solution stop condition the control unit controls the pump such that the pump rate is optimized based on whether a second overheating criterion is satisfied, the second overheating criterion being satisfied when the temperature measured at a temperature sensor exceeds a second predetermined threshold temperature value for longer than a predetermined threshold time duration.

14. The solution circuit apparatus of claim 1, wherein the at least one valve of the switching device comprises a first 2-way valve on the bypass branch and a second 2-way valve on the delivery branch.

15. The solution circuit apparatus of claim 1, wherein the at least one valve of the switching device comprises a 4-way valve configured to interrupt alternately one of the bypass branch and the delivery branch.

16. Blood purification system comprising the solution circuit apparatus of claim 1 and an extracorporeal blood circuit, wherein the control unit is further configured to set the blood purification system into one of a therapy delivery condition and a therapy stop condition, the therapy delivery condition comprises the solution delivery condition, and the therapy stop condition comprises the solution stop condition.

17. Blood purification system according to claim 16, wherein the blood purification system is configured to perform at least one of plasma exchange therapy, pre-dilution hemofiltration, post-dilution hemofiltration, pre-dilution hemodiafiltration, post-dilution hemodiafiltration, or hemodialysis.

* * * * *